(12) United States Patent
Sprague et al.

(10) Patent No.: US 11,882,217 B1
(45) Date of Patent: Jan. 23, 2024

(54) SURGICAL ROBOTIC TOOL AUTHORIZATION SYSTEM

(71) Applicant: Verily Life Sciences LLC, South San Francisco, CA (US)

(72) Inventors: Brandon Sprague, Santa Clara, CA (US); Michelle Gumport, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 157 days.

(21) Appl. No.: 17/302,270

(22) Filed: Apr. 29, 2021

Related U.S. Application Data

(60) Provisional application No. 63/018,149, filed on Apr. 30, 2020.

(51) Int. Cl.
| | |
|---|---|
| H04L 9/32 | (2006.01) |
| A61B 34/30 | (2016.01) |
| H04L 9/08 | (2006.01) |
| A61B 34/00 | (2016.01) |
| H04L 9/40 | (2022.01) |
| A61B 34/35 | (2016.01) |

(52) U.S. Cl.
CPC ............. *H04L 9/321* (2013.01); *A61B 34/25* (2016.02); *A61B 34/30* (2016.02); *A61B 34/35* (2016.02); *H04L 9/0894* (2013.01); *H04L 63/0442* (2013.01)

(58) Field of Classification Search
CPC ...... G06F 21/604; G06F 21/121; G06F 21/44; H04L 9/32; H04L 9/321; H04L 9/08; H04L 9/0894; H04L 63/04; H04L 63/0442; H04L 63/0428; H04L 63/10; H04L 63/101; H04L 63/102; H04L 63/107; A61B 34/25; A61B 34/30; A61B 34/35

See application file for complete search history.

(56) References Cited

U.S. PATENT DOCUMENTS

| | | | |
|---|---|---|---|
| 9,417,625 | B2 | 8/2016 | Graca et al. |
| 9,554,864 | B2 | 1/2017 | Taylor et al. |
| 9,795,453 | B2 | 10/2017 | Tierney et al. |
| 2002/0038118 | A1 | 3/2002 | Shoham |
| 2003/0109780 | A1 | 6/2003 | Coste-Maniere et al. |
| 2006/0009879 | A1 | 1/2006 | Lynch et al. |
| 2015/0202014 | A1 | 7/2015 | Kim et al. |
| 2015/0366624 | A1 | 12/2015 | Kostrzewski et al. |
| 2015/0379441 | A1* | 12/2015 | Syed ............... G16H 40/40 705/2 |

(Continued)

*Primary Examiner* — Shaqueal D Wade-Wright
(74) *Attorney, Agent, or Firm* — Kilpatrick Townsend & Stockton LLP

(57) ABSTRACT

Systems and methods for authenticating surgical tools for use in a surgical operation by a robotic surgical system are described herein. The authentication systems and methods include status lists for surgical tools associated with surgical systems. The status lists indicate an allowed or disallowed status of each surgical tool. The status list is stored on a cloud-computing system and shared with various surgical systems at different geographic locations. Prior to performing a surgical operation or at other times, the surgical systems decrypt tool data received from a surgical tool to access identifying information and access a tool status from the status list based on the tool data. The surgical systems then proceed based on the status of the surgical tool in the status list.

35 Claims, 7 Drawing Sheets

(56) References Cited

U.S. PATENT DOCUMENTS

| | | |
|---|---|---|
| 2018/0014894 A1 | 1/2018 | Hagag et al. |
| 2018/0049822 A1 | 2/2018 | Henderson et al. |
| 2018/0049833 A1 | 2/2018 | Shelton, IV et al. |
| 2019/0201117 A1* | 7/2019 | Yates ............... A61B 34/76 |
| 2019/0201138 A1 | 7/2019 | Yates et al. |
| 2019/0207911 A1* | 7/2019 | Wiener ............ G16H 80/00 |
| 2019/0374292 A1* | 12/2019 | Barral ............... B25J 9/1682 |
| 2021/0251720 A1* | 8/2021 | Jhaveri .......... G06K 19/0723 |

\* cited by examiner

SURGICAL ROBOTIC TOOL AUTHORIZATION SYSTEM

CROSS-REFERENCE TO RELATED APPLICATIONS

This application claims priority to U.S. Provisional Patent Application No. 63/018,146, filed Apr. 30, 2020 entitled "Surgical Robotic Tool Authorization System," the entirety of which is hereby incorporated by reference.

BACKGROUND

In recent years, robotic surgeries have become increasingly popular because of their advantages over traditional human-operated open surgeries. Surgical tools used in robotic surgeries enable a human surgeon to have improved levels of dexterity, range of motion, and precision. In most robotic surgical systems, these tools are connected to robotic arms and interchangeable depending on the surgery to be performed.

SUMMARY

Various examples are described including systems, methods, and devices relating to configuring surgical robots.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by a data processing apparatus, cause the apparatus to perform the actions. One general aspect includes a computer-implemented method, including storing, in a memory of a computing device of a surgical system, a first device key specific to a surgical tool coupled to a surgical system. The computer-implemented method also includes receiving, via a communication device of the computing device and from the surgical tool, an authentication message encrypted with a second device key specific to the surgical tool. The computer-implemented method further includes authenticating the surgical tool based on a key pair authentication to decrypt the authentication message using the first device key. The computer-implemented method also includes receiving, via the communication device of the computing device and from the surgical tool, tool data including an identifier of the surgical tool. The computer-implemented method also includes determining a status result based on the identifier and a status list, the status list including identifiers and use locations for a plurality of surgical tools. The computer-implemented method also includes performing an action using the surgical system based on the status result. Other examples of this aspect include corresponding computer systems, apparatuses, and computer programs recorded on one or more computer storage devices, each configured to perform the actions of the methods.

Another general aspect includes a robotic surgical system, including a plurality of robotic arms to receive surgical tools. The robotic surgical system also includes a communication device communicatively coupled to the plurality of robotic arms, the communication device configured to communicate with a surgical tool when the surgical tool is connected to one of the plurality of robotic arms. The robotic surgical system also includes one or more processors and one or more computer-readable media including processor-executable instructions that, when executed by the one or more processors, cause the one or more processors to store a first device key specific to the surgical tool and receive, via the communication device and from the surgical tool after the surgical tool is coupled to the robotic surgical system, an authentication message encrypted with a second device key. The instructions further cause the one or more processors to authenticate the surgical tool based on a key pair authentication operation to decrypt the authentication message using the first device key. The instructions further cause the one or more processors to receive, via the communication device and from the surgical tool, tool data including an identifier of the surgical tool and to determine a status result based on the identifier and a status list, the status list including identifiers and use locations for a plurality of surgical tools. The instructions further cause the one or more processors to perform an action using the robotic surgical system based on the status result. Other examples of this aspect include corresponding computer systems, apparatus, and computer programs recorded on one or more computer storage devices, each configured to perform the actions of the methods.

Another general aspect includes a non-transitory computer-readable storage device including computer-executable instructions that, when executed by a computer system, cause the computer system to perform operations including: store a first device key specific to a surgical tool coupled to a surgical system. The instructions also cause the computer system to receive, via a communication device of the computing system and from the surgical tool, an authentication message encrypted by a second device key specific to the surgical tool and authenticate the surgical tool based on a key pair authentication operation using the first device key and the authentication message. The instructions further cause the computer system to receive, via the communication device of the computing system and from the surgical tool, tool data including an identifier of the surgical tool and determine a status result based on the identifier and a status list, the status list including identifiers and use locations for a plurality of surgical tools. The instructions further cause the one or more computing systems to perform an action using the surgical system. Other examples of this aspect include corresponding computer systems, apparatus, and computer programs recorded on one or more computer storage devices, each configured to perform the actions of the methods.

Another general aspect includes a computer-implemented method, including storing, in a memory of a computing device of a surgical system, a first device key specific to a surgical tool coupled to the surgical system and receiving, via a communication device of the computing device and from the surgical tool, an authentication message encrypted with a second device key. The computer-implemented method also includes authenticating, at the computing device, the surgical tool based on decrypting the authentication message with the first device key. The computer-implemented method also includes receiving, at the computing device and from the surgical tool, tool data including an identifier of the surgical tool and determining a status result based on the identifier and a surgical tool blacklist, the status result identifying a match between the identifier and a portion of the surgical tool blacklist, the surgical tool blacklist including identifiers and status data describing an allowed or disallow status of each surgical tool. The computer-implemented method also includes disabling at least one function of the surgical system based on the status result. Other examples of this aspect include corresponding computer systems, apparatus, and computer programs recorded on one or more computer storage devices, each configured to perform the actions of the methods.

Another general aspect includes a computer-implemented method, including storing, at an authentication server, a status list including identification data and status data for a plurality of surgical tools and storing, at the authentication server, a tool use dataset including the identification data and location data associated with the plurality of surgical tools, the location data representative of locations at which the plurality of surgical tools have been used. The computer-implemented method also includes receiving tool connection data from a robotic surgical system, the tool connection data describing a first identity of a first surgical tool and a first location of the first surgical tool in response to the first surgical tool being connected to the robotic surgical system. The computer-implemented method also includes determining a result by comparing the tool connection data with the tool use dataset. The computer-implemented method also includes generating an updated status list based on the result and transmitting the updated status list to a plurality of different robotic surgical systems, where the plurality of different robotic surgical systems are configured to use the updated status list to authenticate surgical tools. Other examples of this aspect include corresponding computer systems, apparatus, and computer programs recorded on one or more computer storage devices, each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
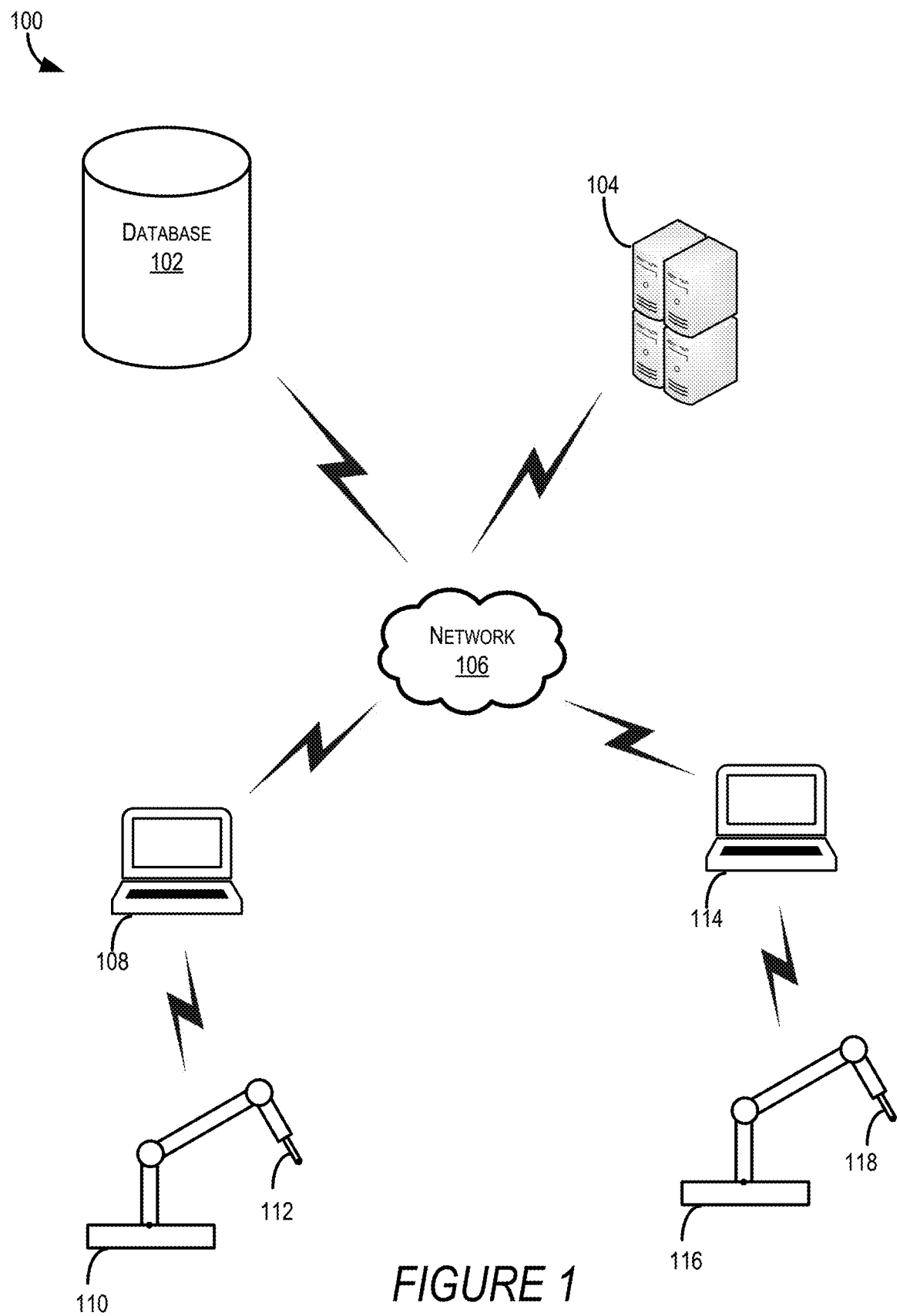
FIG. 1 illustrates a block diagram illustrating an example system for implementing a surgical tool authorization system, according to at least some examples.

Examples are described herein in the context of configuring a surgical robot at the start of and throughout surgical procedures. Those of ordinary skill in the art will realize that the following description is illustrative only and is not intended to be in any way limiting. For example, the techniques described herein may be used to initially authorize surgical tools to ensure surgical tools are not cloned or used in unauthorized manners, including disabled tools that are the subject of recalls or expired lifespans. Though examples and techniques are described with reference to authorization lists (e.g., blacklists or whitelists) for surgical tools, the methods described herein may be implemented in other robotic systems such as robotic systems used in assembly processes or other user-controlled robotic systems. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a robotic surgical system includes multiple robotic arms that each receive a surgical tool. An authorization system according to the following description prevents the use of unapproved clone tools, unauthorized tools, expired tools, recalled tools, or other surgical tools that a manufacturer or system manager may want to block from use with the robotic surgical system. In addition to typical authentication steps performed when a surgical tool is connected to a robotic arm of a robotic surgical system, an additional authentication step includes receiving encrypted tool data from the surgical tool when connected to the surgical system. The tool data is decrypted and compared with a database of information about surgical tools. The database may, for example, include a blacklist identifying surgical tools that are not authorized for operation during a surgical procedure. The blacklist may include identifiers of surgical tools that have been identified for blocking or preventing use. The blacklist may, in some cases, instead be a whitelist including identifiers of surgical tools that are allowed for use with a surgical tool system, and only surgical tools identified on the whitelist are enabled for use. The blacklist is maintained in a remote cloud-based computer and pushed out to multiple different robotic surgical systems. If a connected surgical tool is identified on a blacklist, the surgical system may block or prevent one or more functions of the surgical tool, for example, by preventing use of the surgical tool in a surgical operation. Similarly, if a surgical tool does not respond with encrypted tool data, the robotic surgical system may prevent the surgical tool from being used.

Generally, the authentication process described herein is performed when a surgical tool is connected to the surgical system. The process includes a computer of the surgical system receiving identifying information and other surgical tool data from the surgical tool when the tool is connected to the surgical system. The surgical tool conveys identifying information to the computer system of the surgical system. The identifying information uniquely identifies the surgical tool and can also include usage data describing the remaining life, an end of life data, an indication of the number of uses the surgical tool has been through, etc. In some examples, a set of numbers associated with the surgical tool may identify the surgical tool, e.g., a combination of multiple values that collectively form a unique signature for the device, such as a lot number plus an identifier within the lot (not globally unique, but unique per lot) plus the production rate and production location. For example, an identifier may include a first set of codes indicating a tool type, a second set of codes indicating a tool size, a third set of codes indicating a tool manufacturer, a fourth set of codes indicating a manufacturing location, and a fifth set of codes indicating a manufacturing date. The computing system then compares the identifying information against a local copy of a cloud-stored status list indicating a status of a number of surgical tools. The status list may indicate that a surgical tool is authorized for use or has been blacklisted to prevent use. If the surgical tool is whitelisted or authorized, then it may be used in a surgical operation. If the surgical tool is blacklisted, then the surgical tool may be prevented from functioning and used during a surgical operation.

In addition to identifying information, the surgical tool may also store authentication information. For example, the surgical tool may have a first key stored in a memory of the surgical tool that can be used with a second key stored or accessed by the computing system of the surgical system and used for key pair authentication to authenticate and decrypt the surgical tool data. The key pair authentication may be performed to decrypt the identifying information and tool data received from the surgical tool. The surgical tool authentication system provides a safeguard against cloned or unapproved surgical tools including black-market surgical tools or surgical tools using cloned valid tool certificates. The system also provides a mechanism for deactivating surgical tools that are being removed from use due to an end of their useful life, a recall, a tool replacement, or other surgical tool life cycles. Evidence of improper use may be identified by identifying multiple locations or surgical systems in different locations authenticating surgical tools with identical certificates or identifying information near in time to each other. This may, for example indicate that a certificate has been cloned and is being used to authorize disallowed, unapproved, or otherwise counterfeit tools. A computing system, such as a remote computing device or a cloud computing system, generates the status list by first receiving identifying information and usage data for any surgical tools in use at different surgical systems and then identifying any surgical tools whose identifying information appears as being associated with more than one surgical system or more than one location substantially simultaneously. Surgical tools that appear to be used in multiple locations may instead identify instances of cloned tool certificates or unapproved surgical tools that are otherwise counterfeit. In some instances, the surgical tool authentication system may also be useful for blacklisting or preventing use of surgical tools that have been recalled or otherwise marked for discontinued use.

Additionally, surgical tools that have a useful life may be shut off or deactivated after a predetermined threshold number of uses is reached or a useful life is entirely consumed. For example, different surgical tools may have a predetermined number of uses or usage time before a manufacturer or other entity determines that the useful life of the surgical tool has expired. In some examples, the be deactivated or disallowed for use with a surgical system after reaching a predetermined threshold, such as eighty percent of the useful life of the surgical tool.

Turning now to the figures, FIG. 1 illustrates a block diagram illustrating an example system 100 for implementing a surgical tool authorization system, according to at least some examples. The system 100 includes a database 102, a remote computing system 104, a network 106, a surgical computing system 108, a surgical system 110, a second surgical computing system 114, and a second surgical system 116. Generally, the remote computer system 104 may be a server or distributed computing system and is set up to manage authentication of surgical tools connected to surgical systems 110 and 116 over the network 106 as well as generate, maintain at the database 102, and distribute copies of the status list to surgical systems 110 and 116.

The remote computing system 104 generates the status list based on surgical tool data received from surgical systems 110 and 116. The surgical tool data may include a tool identifier such as a unique identifier, serial number, or series of identifying characters to identify the surgical tool. The surgical tool data may include identifiers for every surgical tool associated with a surgical system 110 and 116. The surgical tool data may also include use data indicating a number of uses or a remaining number of uses in the lifetime of the surgical tool. The status list includes a list of surgical tools with an indication of whether they're in use or not and whether the surgical tool is allowed or disallowed. The disallowed status may include an indication for surgical tools 112 and 118 which have tool identifying information associated with multiple surgical systems at the same time or multiple surgical systems at different locations such as different hospitals. For example, the surgical computing system 108 and the second surgical computing system 114 may convey identifying information for an identical surgical tool to the remote computing system 104 but be located in different hospitals or each indicate that the identical surgical tool was used simultaneously. The status list may also include a disallowed status for recalled surgical tools 112 or surgical tools 112 that have reached the end of their lifecycle. In some examples, the remote computing system 104 may determine or identify surgical tools 112 for which the use counter, indicating the number of uses or remaining life of the surgical tool 112, is not incrementing with each use, potentially indicating false or counterfeit surgical tool data. In some examples, the status list may be a whitelist indicating surgical tool identities authorized for use. In some examples, the status list may be a blacklist indicating surgical tool identities not authorized for use. Though examples may be described with respect to a blacklist or a whitelist, it is intended that either a blacklist or a whitelist may be implemented. In some examples, the status list may include a list of surgical tools and an allowed or disallowed status for each. The status list may be stored in the database 102 and conveyed or distributed to surgical systems. The status list may be distributed each time the status list is updated or at regular intervals.

The database 102, remote computing system 104, surgical computing system 108, and surgical system 110 communicate over network 106. The network 106 includes communication channels wired and wireless for communications between devices, such as the surgical computing system 108 and remote devices such as between the remote computing system 104 and the database 102. The network 106 may include a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

The surgical systems 110 and 116 are robotic surgical systems with the surgical computing system 108 and 114 including the surgical console of the robotic surgical system as described in further detail with respect to FIG. 2 below.

In operation, a surgical system 110, 116 receives one or more surgical tools 112 and 118 that are installed in one or more surgical arms of the surgical system 110, 116. The surgical systems 110 and 116 are shown with a single robotic arm but may each include multiple robotic arms, each receiving a surgical tool. Though the following description discusses the surgical system 110 and the surgical computing system 108, the description is equally applicable to the second surgical system 116 and the second surgical computing system 114.

When a surgical tool 112 is connected to a surgical system 110, the surgical tool 112 conveys surgical tool data to the surgical computing system 108 over the network 106, e.g., in response to a request from the surgical computing system 108 or as an unsolicited message sent upon the tool detecting it was inserted into a robotic surgical system. In some examples, the surgical tool conveys the surgical tool data to the surgical computing system 108 over a separate network than the network 106 used for communication between the remote computing system 104 and the surgical computing system 108. For example, during a surgical operation, connection between the surgical computing system 108 and the remote computing system 104 or any other remote systems may be disabled to prevent interference during the surgical operation or network traffic may be limited to verifying installed surgical tools. In such instances, the network 106 may include multiple different networks, such as a local wired network for communications between the surgical tool 112, the surgical system 110, and the surgical computing system 108. In some examples, the surgical system 110 may include the surgical computing system 108 and therefore the communications between the surgical system 110 and the surgical computing system 108 may be within a single device. The surgical tool 112 may exchange certificates and validity challenges with the surgical system 110 and the certificates may be validated on the surgical computing system 108, in some examples, certificate validation and validation challenges may be performed with the remote computing system 104.

The surgical computer system 108 stores a local copy of a status list, received from the remote computing system 104 over the network 106, indicating an allowed or disallowed status of various surgical tools. The status list may be generated by the remote computing system 104 based on surgical tool data received from multiple surgical systems. The status list may include a disallowed status indication for surgical tools 112 which have identifying information associated with multiple surgical systems. The status list may also include a disallowed status, a number of uses, a useful life, a use clock, a batch number, a manufacturing location, and a use location. The use location may include a hospital or surgical center location, a surgical room location, a specific surgical system, or any combination thereof In some examples, the remote computing system 104 may determine or identify surgical tools for which the use counter, indicating the number of uses or remaining life of the surgical tool, is not incrementing with each use, potentially indicating false or counterfeit surgical tool data. The status list may be stored in the database 102 and conveyed or distributed to surgical systems. The status list may be distributed each time the status list is updated or at regular intervals.

Upon receiving the surgical tool data from the surgical tool 112, the surgical computer system 108 determines a status of the surgical tool 112 based on the status associated with the surgical tool data within the status list. In some examples, the status list may be a whitelist indicating surgical tool identities authorized for use. In some examples, the status list may be a blacklist indicating surgical tool identities not authorized for use. In some examples, the status list may include a list of surgical tools and an allowed or disallowed status for each.

When the surgical computer system 108 determines that the surgical tool 112 is allowed for use based on the status list, the surgical system 110 may proceed with a surgical operation using the surgical tool 112. When the surgical computer system 108 determines that the surgical tool 112 is disallowed for use, the surgical system 110 may proceed with the surgical operation without the use of the surgical tool 112, or in some examples, the surgical system 110 may not proceed with the surgical operation until all surgical tools 112 are authorized for use.

The description of FIG. 1 has been described according to a particular configuration, but should not be construed as limiting the scope of the present disclosure. Additional examples are provided and described below describing examples and implementations of various elements described generally with respect to FIG. 1.

Figure 2:
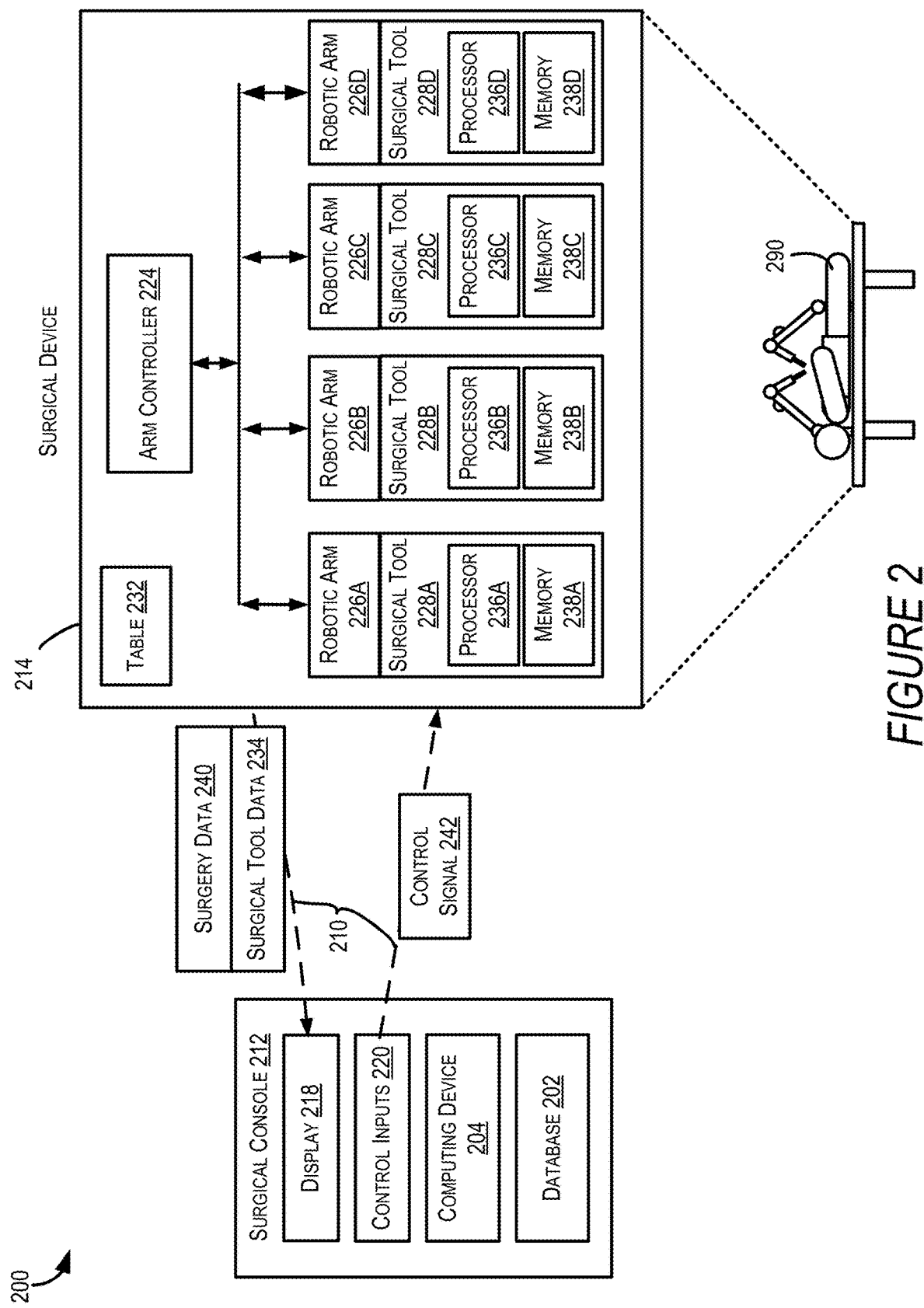
FIG. 2 illustrates an example system for authenticating surgical tools connected to a robotic surgical system, according to at least some examples.

FIG. 2 illustrates a system 200 for authenticating surgical tools connected to a robotic surgical system, according to at least some examples. The system 200 may include the surgical system 110, surgical computing system 108, and surgical tool 112 described with respect to FIG. 1. In the system 200, the surgical device 214 is configured to operate on a patient 290. The system 200 also includes a surgical console 212 connected to the surgical device 214 and configured to be operated by a surgeon to control and monitor the surgeries performed by the surgical device 214. The system 200 might include additional stations (not shown in FIG. 2) that can be used by other personnel in the operating room, for example, to view surgical information, image data, etc., sent from the surgical device 214. The surgical device 214, the surgical console 212, and other stations can be connected directly or through the network 210, such as a local-area network ("LAN"), a wide-area network ("WAN"), the Internet, or any other networking topology known in the art that connects the surgical device 214, the surgical console 212 and other stations.

The surgical device 214 can be any suitable robotic system that can be used to perform surgical procedures on the patient 290. The surgical device 214 includes one or more robotic arms 226A-D (which may be referred to herein individually as a robotic arm 226 or collectively as the robotic arms 226) connected to a base such as a table 232. The robotic arms 226 may be manipulated by control inputs 220, which may include one or more user interface devices, such as joysticks, knobs, handles, or other rotatable or translatable devices to effect movement of one or more of the robotic arms 226. The surgical device 214 includes an arm controller 224 to control the positioning and movement of the robotic arms 226 based on a control signal 242 from the surgical console 212 generated by the control inputs 220.

The robotic arms 226A-D may be equipped with one or more surgical tools 228A-D to perform aspects of a surgical procedure. For example, the robotic arms 226A-D may be equipped with surgical tools 228A-D, (which may be referred to herein individually as a surgical tool 228 or collectively as the surgical tools 228). The surgical tools 228 can include, but are not limited to, tools for grasping for holding or retracting objects, such as forceps, graspers and retractors, tools for suturing and cutting, such as needle drivers, scalpels and scissors, imaging and viewing tools such as cameras and endoscopes, and other tools that can be used during a surgery. Each of the surgical tools 228 can be controlled by the surgeon through the surgical console 212 including the control inputs 220.

Each of the surgical tools 228 includes a processor 236 and a memory 238. The processor 236 may include an application specific integrated circuit, or one or more other types of processors according to this disclosure. The processor 236 may function as or be coupled with a communication device of the surgical tool to convey surgical tool data 234 to the surgical computing system 108. In some examples, the communication device may be embodied in the surgical computing system 108 that accesses the surgical tool data 234 stored on the memory 238. The memory 238 stores data and is accessible by the processor 236. The memory 238 stores the surgical tool data 234 as well as authenticating information, such as a first device key, for use in authenticating and decrypting the surgical tool data, which may be performed by the computing device 204. The data stored in the memory 238 may be encrypted, the memory 238 may be a secure memory, or may be unencrypted. When the surgical tools 228 are connected to the robotic arms 226, which may include both physical and data connections, the processor 236 may convey the surgical tool data 234 to the computing device 204 over the network 210. In some examples, the surgical tools 228 may include only a memory 238 that is readable by the computing device 204 through a data connection to the surgical tools 228 through the robotic arms 226.

Different surgical devices may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one surgical device 214 is depicted, any suitable number of surgical devices 214 may be employed within system 200.

The surgical console 212 includes a display 218 for providing a feed of image data from a camera as well as other surgery information and surgery data 240 during a surgical procedure. The surgery data 240 from the surgical device 214 is transferred to the surgical console 212 over the network 210. The surgical tool data 234 is also transferred to the surgical console 212 over the network 210. The computing device 204 described in FIG. 2 is shown included in the surgical console 212 but may also be located remotely of the surgical console 212 as described above. Additionally, the database 202, which may include a second device key for key pair authentication with the first device key of the surgical tool 236 as well as a local copy of the status list indicating a status for a plurality of surgical tools. The surgical console 212, and specifically the computing device 204 may determine the status of each of the surgical tools 228 based on the surgical tool data 234 and the local copy of the status list. Based on the status of each of the surgical tools, the control signal 242 may then operate one or more functions of the surgical tools 228.

Figure 3:
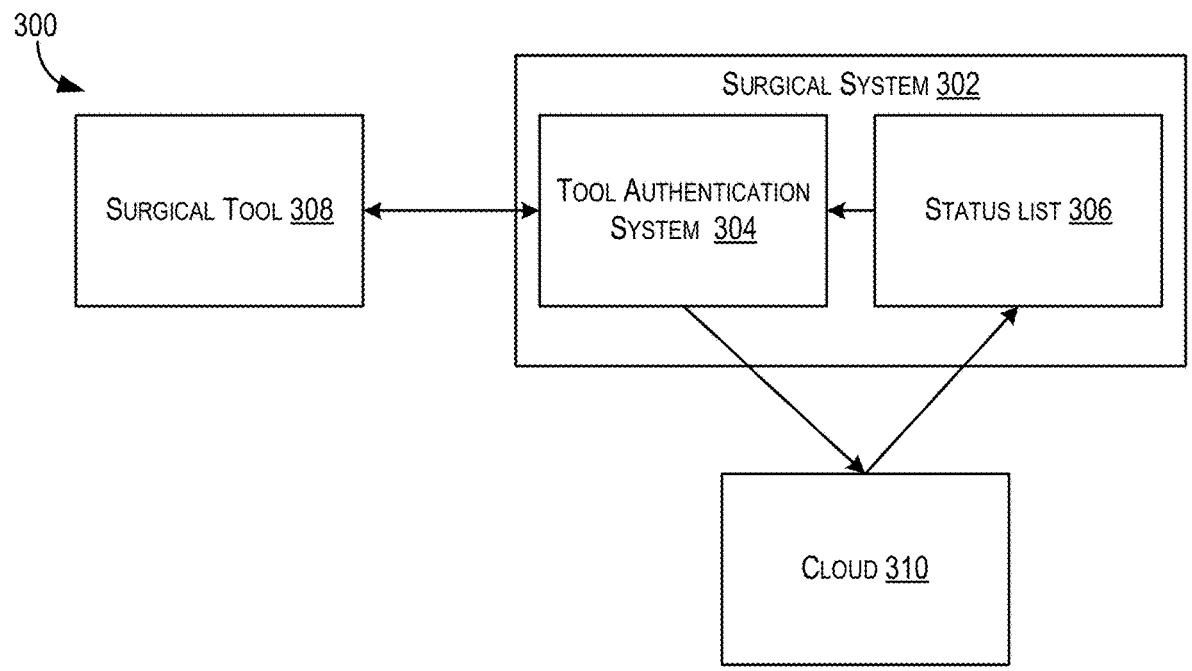
FIG. 3 illustrates a block diagram illustrating a surgical tool authorization system, according to at least some examples.

FIG. 3 illustrates a block diagram 300 illustrating a surgical tool authorization system according to at least some examples. The block diagram 300 illustrates a surgical system 302, which may be the surgical system 110 of FIG. 1. The surgical system 302 includes a tool authentication system 304 that includes a processor and memory for authenticating surgical tools, which may be part of the surgical computing system 108 and a status list 306. The tool authentication system 304 may include instructions and a status list 306 that may both be stored on and part of a computing device of the surgical system 302 such as a surgical console with a computing device included therein. The block diagram 300 also includes a cloud computing system 310 which may include the remote computing system 104 and the database 102 of FIG. 1.

In operation, a surgical tool 308 is connected to the surgical system 302 while setting up for a surgical operation using the surgical system 302. After it is connected, the surgical tool 308 conveys a connection signal to the surgical system 302. The surgical tool 308 and the surgical system 302 exchange certificates as part of an authentication process. The surgical system 302 may validate the tool certificate with the cloud computing system 310. This validation process may include validation challenges from the cloud computing system 310 and answers from the surgical tool 308. Next, the surgical tool 308 conveys surgical tool data to the surgical system 302. The surgical tool data may include the identifying data and usage data described above with respect to FIG. 1. The surgical tool data may be encrypted when conveyed to the surgical system 302. The surgical tool data may be encrypted with a second device key to secure the surgical tool data, the encrypted surgical tool data may be decrypted using the first device key through key authentication. While key-pair authentication mechanisms have been discussed above, e.g., elliptic curve key pairs, any suitable authentication mechanism may be used.

After decrypting the surgical tool data, the tool authentication system 304 determines a status of the surgical tool 308 based on the status list 306. The surgical system 302 may proceed with authentication of the surgical tool 308 based on the surgical tool data and the key pair authentication as well as the status list 306. In an example, the remote computing system 310 may compare the surgical tool data against a master status list and determine whether the surgical tool 308 has been used, or certificates associated with the surgical tool 308 have been used, in association with different surgical systems.

Following a surgical operation, the tool authentication instructions 304 conveys the surgical tool data to the remote computing system 310 with the identifying information for the surgical tool 308 as well as identifying information for the surgical system 302. The remote computing system 310 then updates a master status list stored on the remote computing system 310 based on the surgical tool data and the identifying information for the surgical system 302. Additionally, the remote computing system 310 may determine whether the use counter or useful life of the surgical tool 308 has reached a threshold indicating a lifetime of use of the surgical tool 308. The identification of a surgical tool 308 associated with multiple different surgical systems or identification that a lifetime of the surgical tool 308 has expired may result in the remote computing system 310 updating the master status list indicating the surgical tool 308 is disallowed. The master status list may then be distributed to various cloud-connected surgical systems 302 as status list 306.

Figure 4:
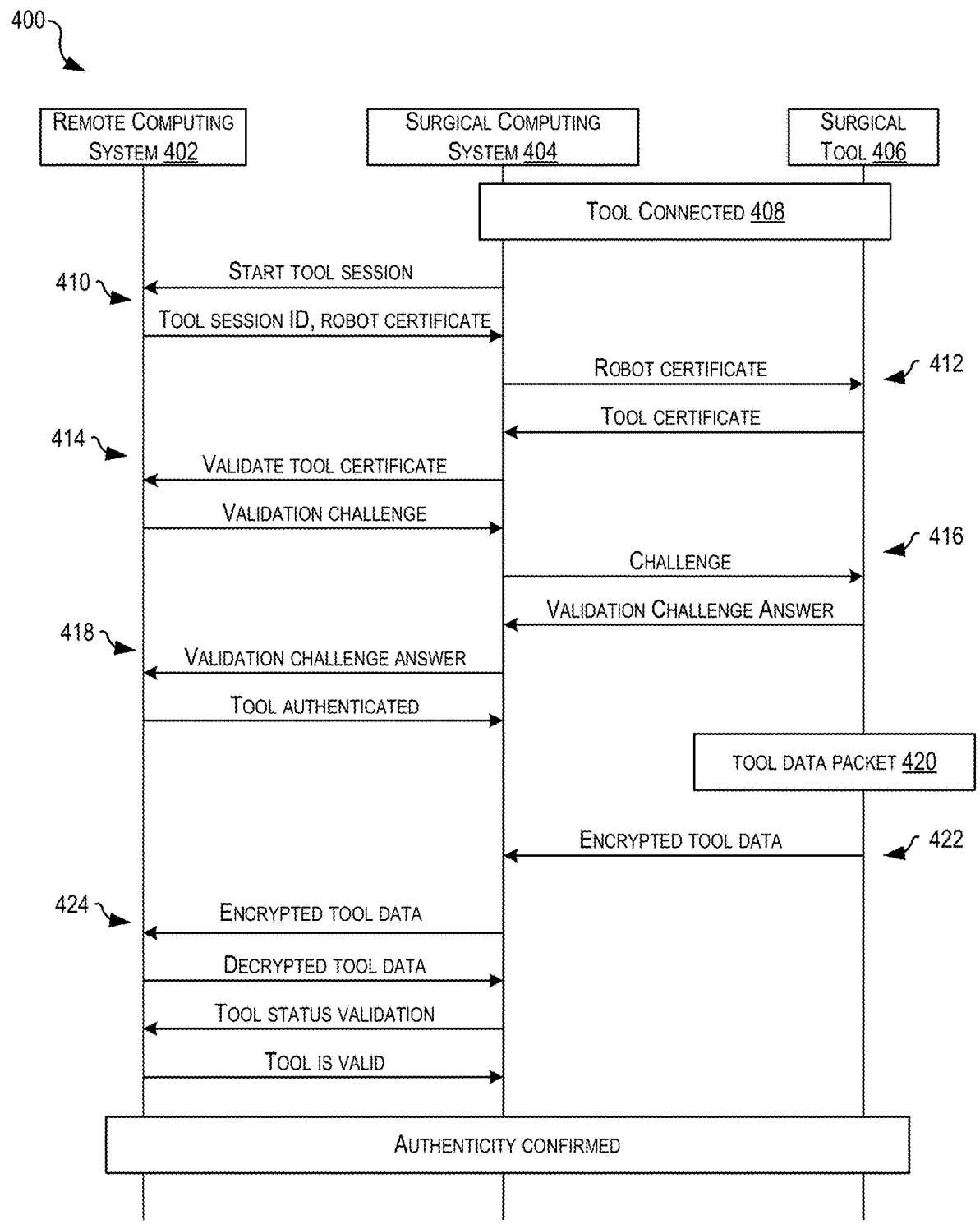
FIG. 4 illustrates a communication diagram showing a flow of communications for authorizing a surgical tool, according to at least some examples.

FIG. 4 illustrates a communication diagram showing a flow of communications for authorizing a surgical tool, according to at least some examples. The communication diagram 400 illustrates communications between a surgical tool, such as the surgical tool 112 or surgical tool 308 of FIG. 1 or 2, a surgical computing system 108, and a remote computing system such as the remote computing system 104. In some instances, the remote computing system 402 may include a computing system of the robotic surgical device connected to the remote computing system 104. The communications include the authorization steps performed after connecting a tool to the surgical system.

At 408, the surgical tool 406 is connected to the surgical system. The connection may include physical connections as well as data coupling over a communication channel such as a wired or wireless communication channel.

At 410, the surgical computing system 404 conveys a start tool session signal to the remote computing system 402. In response, the remote computing system 402 returns a tool session identifier and a certificate for the surgical system 302.

At 412, the surgical computing system 404 conveys the certificate for the robotic surgical system to the surgical tool 406. In response, the surgical tool may return a tool certificate to the surgical computing system 404.

At 414, the control computing system communicates a validation signal to the remote computing system 402. The validation signal may include an indication that the surgical tool has been connected and includes the tool certificate from the surgical tool 406. In response, the remote computing system 402 returns a validation challenge to the surgical computing system 404.

At 416, the surgical computing system 404 provides a challenge, based on the validation challenge, to the surgical tool 406. The surgical tool 406 returns an validation challenge answer to the validation challenge which is then conveyed to the remote computing system 402 at 418 from the surgical computing system 404 to complete the validation process. Assuming a match or a proper answer is returned by the surgical tool 406, the remote computing system 442 authenticates, based on only the tool certificate and the challenge answer, the surgical tool 406 for use and conveys a signal to the surgical computing system 404 indicating the surgical tool 406 is authenticated for use. Following the initial authentication, the surgical computing system 404 performs an additional authentication step based on the status list. The authentication performed using the status list is accomplished at 422 and 424, described below.

A tool data packet 420 originates at the surgical tool 406. The surgical tool 406 may receive a request for tool data from the surgical computing system 404, and in response, generate the tool data packet 420. The tool data packet 420 stores information relating to the surgical tool 406 in a format prepared for the surgical computing system 404. In some examples, the surgical tool 406 then encrypts the tool data packet 420 before transmitting it to the surgical computing system 404. For example, the tool data packet 420 may include identifying information such as a serial number, product code, or any other such identifying information as well as usage data for the surgical tool 406. The tool data packet 420 may be encrypted using any suitable encryption method such as symmetric key or public key encryption methods.

At 424, the encrypted tool data in the tool data packet 420 is conveyed to the remote computing system 402. The remote computing system 402 receives and decrypts the tool data using its private key, and returns the decrypted tool data to the surgical computing system 404. The remote computing system 402 may decrypt the tool data packet 420 using a first device key stored at the auxiliary computing system 402. The tool data packet 420 may be decrypted using any known key validation techniques, such as elliptic curve key validation.

The tool data, including at least the identifying information for the surgical tool 406 and the usage data is then used by the surgical computing system 404 to validate the status of the surgical tool 406 following the surgical tool authentication described above. The status of the surgical tool 406 may be validated at the surgical computing system 404 by looking up, on a status list stored at the surgical computing system 404 or at the remote computing system 402, a status for the surgical tool 406 based on the identifying data from the tool data. In some examples the status may indicate an allowed, a disallowed, a recalled, a partially allowed, or other such status. In an allowed status, the surgical tool 406 may be authenticated for use in a surgical operation. In a disallowed status, the surgical tool 406 may be disabled for one or more operations in a surgical procedure. For example, the surgical tool may be entirely deactivated based on the disallowed status or may have certain functionality disabled based on the disallowed status, which may be indicated in a partially allowed status. A recall status may indicate whether the particular surgical tool 406 has been recalled and therefore removed from service by the manufacturer, in which case it is entirely disabled and prevented from use. When the status of the surgical tool 406 is validated, the surgical tool 406 is fully authenticated and prepared for use in a surgical operation. The result of the status from the status list may be used to generate a notification to the user, such as a notification that a tool is accepted, the tool has limited functionality, the tool is subject to a recall, the tool is disabled, or any other status from the status list.

Figure 5:
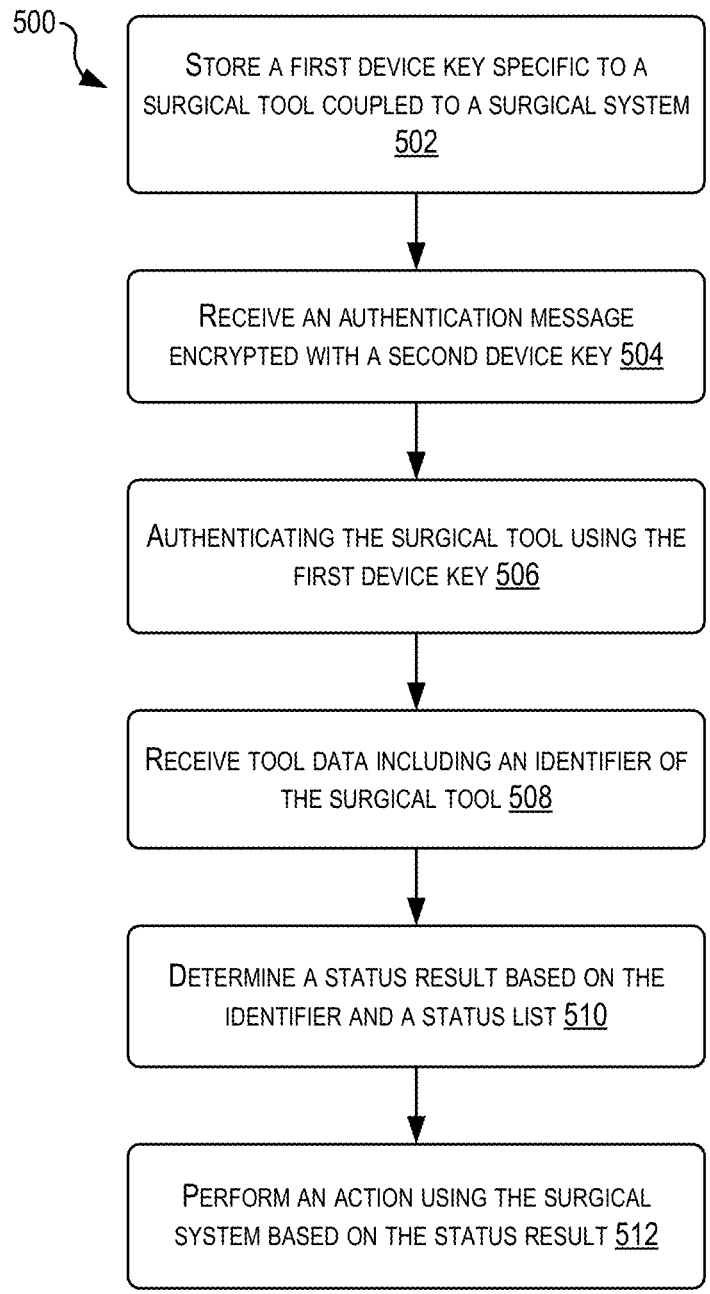
FIG. 5 illustrates an example flow chart depicting an example process for authorizing a surgical tool, according to at least some examples.
Figure 6:
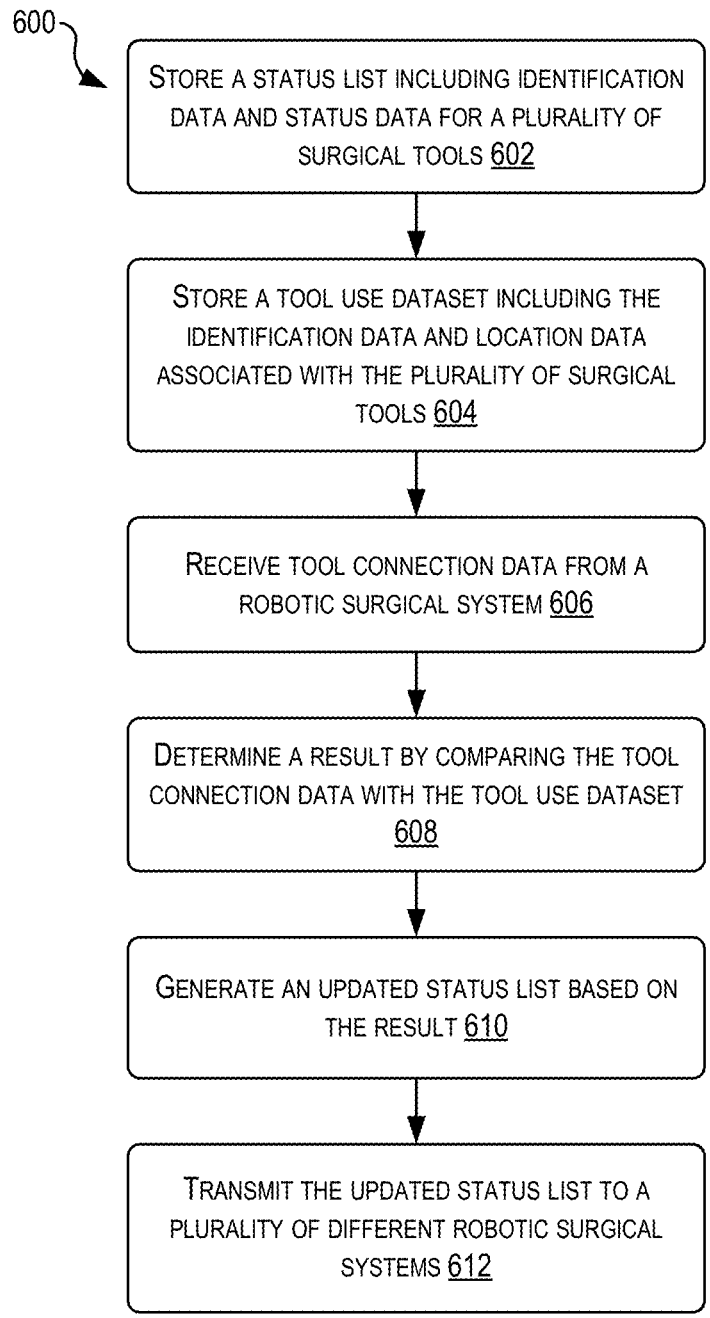
FIG. 6 illustrates an example flow chart depicting an example process for generating and updating an authorization status list, according to at least some examples.

FIGS. 5-6 illustrate example methods for authenticating surgical tools using a surgical tool status list, according to at least some examples. These processes, and any other processes described herein, are illustrated as logical flow diagrams, each operation of which represents a sequence of operations that can be implemented in hardware, computer instructions, or a combination thereof In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Referring now to FIG. 5, FIG. 5 illustrates an example flow chart depicting an example process 500 for authorizing a surgical tool, according to at least some examples. The process 500 is performed by the surgical computing system 108, in connection with the database 102 and remote computing system 104 over the network 106. The surgical computing system 108 may be included in a surgical console.

At 502, the surgical computing system 108 stores a first device key specific to a surgical tool 112 coupled to a surgical system. The first device key is received from a remote computing system, such as the cloud computing system 310 of FIG. 3. The first device key may be distributed with the surgical computing system 108, for example as part of a software package included with a surgical suite purchased together. The first device key may be a public key or a private key may be specific and unique to the surgical tool and the surgical system or may include a public key configured for key pair authentication with a private key associated with the surgical tool.

At 504, the surgical computing system 108 receives an authentication message encrypted with a second device key. The authentication message is received from a surgical tool 112 connected to the surgical computing system 108. The authentication message may include identifying information describing the unique identity of the surgical tool 112. The authentication message may be encrypted using a private key, such as a private key of a manufacturer or distributor, which may be the second device key. The authentication message may also include a certificate signed or encrypted by a trusted entity, such as a manufacturer or distributor of the surgical tool 112.

At 506, the surgical computing system 108 authenticates the surgical tool 112 using the first device key. In some instances, the authentication may include key pair authentication based on the first device key and the second device key. In some examples the authentication may be based on matching of or comparison of the first device key with the second device key. The surgical computing system 108 may authenticate the surgical tool or the authentication message by identifying an entity that signed, such as a manufacturer or distributor of the surgical tool based on the certificate received at 504. The surgical computer system 108 may then access a public key, such as the first device key for that particular entity, and use the public key to decrypt the authentication message and verify the data within the authentication message. In some examples, additional data may be used to verify the identity of the surgical tool, such as a hash value or checksum. The surgical computing system 108 may decrypt the hash value or checksum to verify that the contents of the authentication message, or the surgical tool data in some cases, has not been modified.

At 508, the surgical computing system 108 receives tool data including an identifier of the surgical tool 112 from the surgical tool 112. The tool data may be encrypted using the first device key or other encryption methods. In some examples, the second device key may be transmitted to the surgical computing system 108 with the encrypted tool data in a single transmission.

The tool data describes an identity of the surgical tool 112 as well as usage data corresponding with the surgical tool 112. The identity of the surgical tool 112 may be identified by a unique identifier such as a serial number, unique code, series, or string of unique data. In some examples, a set of numbers associated with the surgical tool 112 may identify the surgical tool 112, e.g., a combination of multiple values that collectively form a unique signature for the device, such as a lot number plus an identifier within the lot (not globally unique, but unique per lot) plus the production rate and production location. For example, an identifier may include a first set of codes indicating a tool type, a second set of codes indicating a tool size, a third set of codes indicating a tool manufacturer, a fourth set of codes indicating a manufacturing location, and a fifth set of codes indicating a manufacturing date. Any combination of such identifying information may be used to identify the surgical tool 112. In addition, the tool data may include usage data, for example, including a counter that increments with each use of the surgical tool in a surgical operation. In some examples, the usage data may include a number of hours or minutes of usage, or a number of actuations of the surgical tool 112. Such usage data may be useful for determining when a surgical tool has reached an end of its useful life, for example by determining that the counter, number of uses, or hours exceeds a predetermined threshold value for each of the usage data types, at which point the surgical tool is retired from use based on age and use.

At 510, the surgical computing system 108 determines a status result based on the identifier and a status list. The status list is an example of the status list described with respect to FIG. 1. The status list describes a status of a number of surgical tools. The status list may include a list of allowed surgical tools, a list of disallowed surgical tools, or a list of partially allowed surgical tools. In some examples, the status list may include a plurality of surgical tools with an allowed or disallowed status indicator for each surgical tool. The surgical computing system 108 may include a local copy of the status list, updated from a master status list stored on a remote computing system. The master list may be generated and updated according to the process 600 described with respect to FIG. 6.

The surgical computing system 108 may determine the status result by looking up the surgical tool 112 within the status list based on the identifying data received from the surgical tool 112. The surgical computing system 108 may also reference a recall status for the surgical tool 112 included in the status list as well as the usage data of the surgical tool 112. When a surgical tool is indicated as recalled, the status may be indicated as disallowed or a separate status within the status list may indicate the recall status of the surgical tool 112.

The usage data of the surgical tool 112 may be compared against stored usage data contained within the status list. The status list may include a series of attributes for each surgical tool 112 such as an identifier, usage history, usage location, usage counter, remaining lifetime, and other such attributes for each of the surgical tools 112. The surgical computing system 108 may compare the usage data of the surgical tool 112 as stored on a memory of the surgical tool against the usage data stored in the status list. The surgical computing system 108 may compare any one attribute, such as the usage history, usage location, usage counter, or other such attributes from the stored data within the surgical tool 112 against a corresponding attribute stored in the status list. In some examples, the surgical computing system 108 may compare multiple attributes of the surgical tool 112 against the stored attributes of within the status list. The stored usage data may, for example, include a usage counter for each surgical tool included on the status list, updated with each update of the master status list. The surgical computing system 108 may identify instances where the usage counter for the surgical tool 112 has not incremented or increased and thereby identify an anomaly with respect to use of the surgical tool 112 that may indicate a counterfeit or cloned packet of tool data. This information may be conveyed to a remote computing system for updating the master status list. In some examples, the surgical computing system 108 may determine whether the usage counter has exceeded a predetermined lifetime threshold. For example, if a threshold number of uses for a particular tool is set at three hundred and the surgical tool 112 is now at three hundred uses according to the usage data, the surgical computing system 108 may disallow the surgical tool 112 even if the recall status and status of the surgical tool are indicated as allowed.

The master list may be subsequently updated to indicate the tool has expired and change the status from allowed to disallowed.

At 512, the surgical computing system 108 performs an action using the surgical system based on the status result. The action may include enabling or disabling at least one function of the surgical tool 112 or surgical system 110 based on the status result. In some examples, the action may include accepting the surgical tool for use with the surgical system in a surgical operation. In some examples, the action may include rejecting the surgical tool as disallowed. In some examples, the action may include rejecting the surgical tool as beyond its useful lifetime. In some examples, the surgical tool may still be movable and directable based on control inputs of the surgical computing device while disabling certain functions. For example, a cutting device or grasping device may have the cutting or grasping feature disabled. In some examples, an endoscope that includes lighting, depth finding, and image capturing features may have the lighting feature or depth finding feature disabled while still allowed to capture image data. Other surgical tools 112 including one or more functions ay have one, some, or all of the functions of the surgical tool 112 disable. For example, if the status result for the surgical tool 112 indicates that the tool is allowed, the surgical computing system 108 may enable the surgical tool 112 for a surgical operation. When the status result for the surgical tool 112 indicates that the tool is disallowed, the surgical computing system may disable use of the surgical tool 112 for a surgical operation. In some examples, the surgical computing system 108 may prevent use of the surgical system 110 when the status of the surgical tool 112 is disallowed. In some examples, the surgical computing system 108 may enable use of the surgical system 110 while disabling use of the surgical tool 112 while other surgical tools may be enabled for use. In some examples, the surgical computing system 108 may generate a notification that the surgical tool 112 is disallowed and output the notification to a display of the surgical system 110.

FIG. 6 illustrates an example flow chart depicting an example process 600 for generating and updating an authorization status list, according to at least some examples. The process 600 is performed by the remote computing system 104, in connection with the database 102 and multiple surgical systems 110 communicatively coupled via the network 106. The remote computing system 104 may include a remote computing device that performs some or all of the operations described herein.

At 602, the remote computing system 104 stores a status list including identification data and status data for a plurality of surgical tools. The status list may be a local copy of a status list or a master copy of the status list as described above with respect to FIG. 5. The status list may include a status, e.g., allowed or disallowed, for each surgical tool on the status list.

At 604, the remote computing system 104 stores a tool use dataset including the identification data for the surgical tools and location data associated with the locations of use of each of the surgical tools. The location data may be uploaded to the remote computing system 104 upon beginning or completing each surgical operation by a surgical system in communication with the remote computing system 104. The location data may include a geographic location, such as a longitude and latitude indicating the physical location of the surgical system. The location data may include a hospital or organization location or identifier associate with each surgical system. In some examples, the location data may also include data describing or identifying the surgical system each surgical tool has been connected to as well as timestamps for the different uses and locations of the surgical tools. The location data may also identify an identify or a location, e.g., street address, of a hospital, surgical center, medical center, or other facility where the surgical tool is in use. The location data may further identify an operating room within the surgical location, and a particular surgical system within an operating room that the surgical tool has been used in connection with.

At 606, the remote computing system 104 receives tool connection data from a robotic surgical system. The robotic surgical system may be a surgical system 110 as described above and may upload the tool connection data during setup, during operation, or after completion of a surgical operation. The tool connection data includes identifying information for each surgical tool connected to the robotic surgical system as well as information identifying the location and identify of the robotic surgical system. The tool connection data may also include tool usage data such as a use counter or hour tracker that counts or maintains a count of uses and durations of use. The use counter may increment with each use up to a threshold set for the lifetime of the tool or may count down from a set number of uses until expiration upon reaching zero. The tool connection data may also indicate a manufacturing location and a manufacturing date, which may be useful for identifying tools that have been recalled.

At 608, the remote computing system 104 determines a result, such as whether a surgical tool is allowed for use or a validation status of the tool, by comparing the tool connection data from 606 with the tool use dataset. Determining the validation status of the tool includes determining when location data associated with a surgical tool data does not match stored location data for the surgical tool. Identifying such mismatches or multiple locations may indicate that a surgical tool has been resold, is a counterfeit tool, is being cloned or spoofed, or is otherwise invalid. In some examples, the location data may partially match, for example when a surgical tool is used with multiple surgical systems in a hospital. In such examples, the remote computing system 104 may identify that the surgical tool is being used within a single hospital and not disallow or update the stats of the surgical tool based on the location data not being a perfect match. The remote computing system 104 may also identify uses of a surgical tool, or surgical tool data at the same time or at different times in multiple locations to aid in identifying cloned tool data. For instance, the same tool data appearing with two locations may indicate a cloned tool. The surgical tool data may not be used simultaneously, and so the status list may store a timestamp of the uses as well as the associated location of each use of each surgical tool to identify non-simultaneous uses of surgical tool data. The result determined by the remote computing system 104 may include determining that the tool connection data matches the stored location data for the particular surgical tool. The determination may be performed by comparing the stored location data against the tool connection data. In some examples, the remote computing system 104 may identify simultaneous uses of a single surgical tool according to the tool connection data from different surgical systems. In some examples, the remote computing system 104 may only identify discrepancies in the location data indicating multiple use locations for a single surgical tool. The remote computing system 104 may also identify other reasons for disallowing tools, such as an expired tool, a tool at the end of its useful life, a recalled tool, and the like which are not dependent on location data, but are dependent on updated information from a surgical tool, for example indicating a current use count of the surgical tool to determine whether the tool has reached its maximum lifetime use count before being disallowed.

At 610, the remote computing system 104 generates an updated status list based on the result. In the case of a surgical tool with location data from the tool connection data not matching the stored location data, the updated status list may include changing a status of the surgical tool from an allowed status to a disallowed status based on the discrepancy in the location data. In other instances, the expiration of a useful life, recall of a surgical tool, or other such information described herein may cause the status list to be updated with a new status for a surgical tool. The status list may also include partially allowed statuses, indicating partial uses of particular surgical tools, for example to allow articulation but not use for cutting or some other operation. The status list may also include recalled statuses for surgical tools that have been recalled. There may additionally be sub-categories for each of the statuses, for example with disallowed statuses including sub-categories indicating a reason for disallowed use including cloned identify information, counterfeit tools, multiple locations of use, multiple locations of simultaneous use, recalled tool, useful life expired, lifetime expired (indicating that a predetermined period of time, e.g., a set number of months or years, has elapsed since the tool was manufactured, and other such sub-categories of disallowed tools. In the case of matching location data, the updated status list may include an updated timestamp for the particular surgical tools indicating their most recent use and location.

At 612, the remote computing system 104 transmits the updated status list to a plurality of different robotic surgical systems. The updated status list may be a new status list or may be an updated master status list. The updated status list may be re-transmitted after each update to the status list, after each upload of tool connection data, at a regular interval, or at any other time. The updated status list may then be used locally by the surgical computing system 108 to determine an allowed or disallowed status for each surgical tool connected to the surgical system, as described with reference to FIG. 5.

Figure 7:
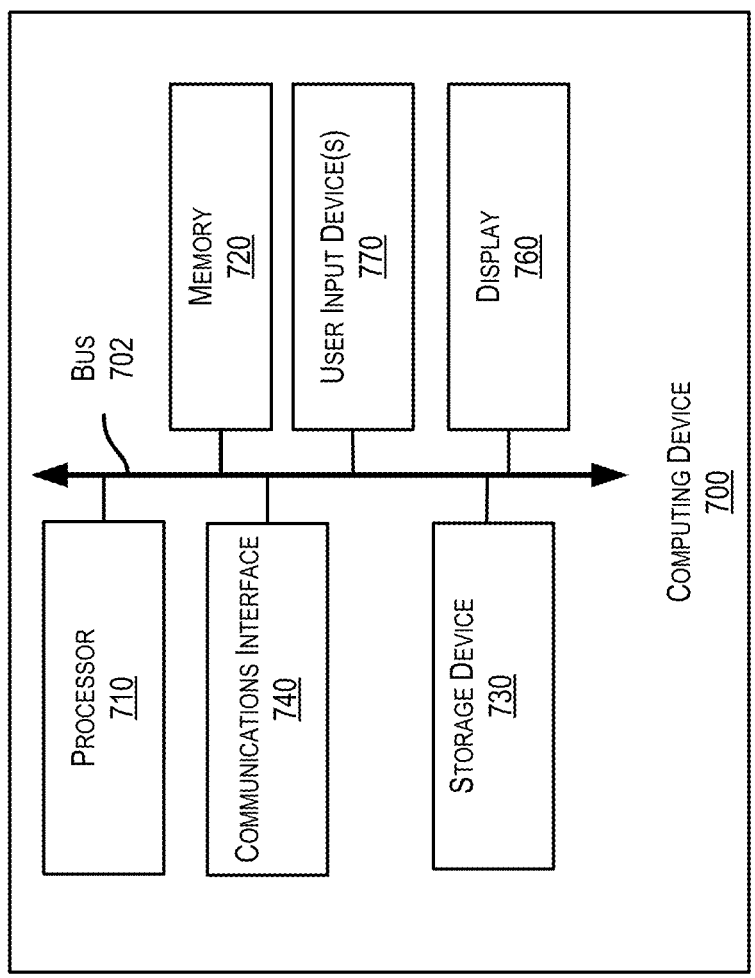
FIG. 7 illustrates a block diagram of a computing device for implementing processes and methods described herein, according to at least some examples.

Referring now to FIG. 7, computing device 700 shows computing device 700 suitable for use in example systems or methods for authenticating surgical tools for use in surgical operations based on a status list. For example, computing device 700 may be the remote computing system 104, surgical computing system 108, second surgical computing system 114, computing device 204 or other computing devices included herein. Computing device 700 includes a processor 710 which is in communication with the memory 720 and other components of the computing device 700 using one or more communications buses 702. The processor 710 is configured to execute processor-executable instructions stored in the memory 720 to perform an authorization check of the surgical tool according to different examples, such as part or all of the example processes 500 and 600 described above with respect to FIGS. 5 and 6. The computing device 700, in this example, also includes one or more user input devices 770, such as a keyboard, mouse, touchscreen, microphone, etc., to accept user input. The computing device 700 also includes a display 760 to provide visual output to a user.

The computing device 700 can include or be connected to one or more storage device 730 that provides non-volatile storage for the computing device 700. The storage device 730 can store system or application programs and data used by the computing device 700, such as software implementing the functionalities provided by the processes 500 and 600. The storage device 730 might also store other programs and data not specifically identified herein.

The computing device 700 also includes a communications interface 740. In some examples, the communications interface 740 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples may be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

While the present subject matter has been described in detail with respect to specific examples thereof, it will be appreciated that those skilled in the art, upon attaining an understanding of the foregoing may readily produce alterations to, variations of, and equivalents to such examples. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more examples of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A computer-implemented method, comprising:
    prior to coupling a surgical tool to a surgical system, receiving, from a remote computing system and at a computing device of the surgical system, a first device key that is specific to the surgical tool;
    storing, in a memory of the computing device of the surgical system, the first device key specific to the surgical tool coupled to the surgical system;
    receiving, via a communication device of the computing device and from the surgical tool, an authentication message encrypted with a second device key specific to the surgical tool;
    authenticating the surgical tool based on the authentication message by decrypting the authentication message with the first device key;
    receiving, via the communication device of the computing device and from the surgical tool, tool data comprising an identifier of the surgical tool;
    determining a status result based on the identifier and a status list, the status list comprising identifiers and use locations for a plurality of surgical tools;
    performing an action using the surgical system based on the status result; and
    providing information about the status result to the remote computing system.

2. The computer-implemented method of claim 1, wherein the action comprises enabling the surgical system to use the surgical tool in a surgical operation.

3. The computer-implemented method of claim 1, wherein determining the status result comprises determining that the status list does not include the tool data, and wherein the action comprises enabling the surgical system to use the surgical tool based on the status list not including the tool data.

4. The computer-implemented method of claim 1, wherein the status result is that the status list includes the tool data, and wherein the action comprises disabling at least one function of the surgical tool based on the status list including the tool data.

5. The computer-implemented method of claim 1, wherein the status result is a first status result and the status list is a first status list, and the method further comprises:
    receiving, from an authentication server, a second status list;

comparing the tool data against the second status list to generate a second result; and enabling the surgical tool for use by the surgical system based on the second result.

6. The computer-implemented method of claim 1, wherein the tool data is encrypted with the second device key, and the method further comprises decrypting the tool data using the first device key.

7. The computer-implemented method of claim 1, wherein performing the action using the surgical system further comprises authenticating the surgical tool based on a key pair authentication operation using the first device key and the second device key.

8. A robotic surgical system, comprising:
a plurality of robotic arms to receive surgical tools;
a communication device communicatively coupled to the plurality of robotic arms, the communication device to communicate with a surgical tool when the surgical tool is connected to one of the plurality of robotic arms;
one or more processors; and
one or more computer-readable media comprising processor-executable instructions that, when executed by the one or more processors, cause the one or more processors to:
prior to coupling the surgical tool to the one of the plurality of robotic arms, receive, from a remote computing system, a first device key that is specific to the surgical tool;
store the first device key;
receive, via the communication device and from the surgical tool after the surgical tool is coupled to the robotic surgical system, an authentication message encrypted with a second device key;
authenticate the surgical tool based on decrypting the authentication message with the first device key;
receive, via the communication device and from the surgical tool, tool data comprising an identifier of the surgical tool;
determine a status result based on the identifier and a status list, the status list comprising identifiers and use locations for a plurality of surgical tools;
perform an action based on the status result; and
provide information about the status result to the remote computing system.

9. The robotic surgical system of claim 8, wherein the action comprises enabling use of the surgical tool in a surgical operation.

10. The robotic surgical system of claim 8, wherein the status result is that the status list does not include the tool data, and wherein the action comprises enabling use of the surgical tool based on the status list not including the tool data.

11. The robotic surgical system of claim 8, wherein the status result is that the status list includes the tool data, and wherein the action comprises disabling at least one function of the surgical tool based on the status list including the tool data.

12. The robotic surgical system of claim 8, wherein the status result is that the status list includes the tool data, and wherein the action comprises generating and presenting a notification via a display of the robotic surgical system in response to the status list including the tool data.

13. The robotic surgical system of claim 8, wherein the status list is maintained on a remote computing device and communicated to the robotic surgical system in response to an update to the status list.

14. The robotic surgical system of claim 8, wherein the first device key is stored on the one or more computer-readable media.

15. A non-transitory computer-readable storage device comprising computer-executable instructions that, when executed by a computer system, cause the computer system to perform operations comprising:
prior to coupling a surgical tool to a surgical system, receive, from a remote computing system, a first device key that is specific to the surgical tool;
store the first device key specific to the surgical tool coupled to the surgical system;
receive, via a communication device of the computing system and from the surgical tool, an authentication message encrypted with a second device key;
authenticate the surgical tool based on decrypting the authentication message with the first device key;
receive, via the communication device of the computing system and from the surgical tool, tool data comprising an identifier of the surgical tool;
determine a status result based on the identifier and a status list, the status list comprising identifiers and use locations for a plurality of surgical tools;
perform an action using the surgical system; and
provide information about the status result to the remote computing system.

16. The computer-readable storage device of claim 15, wherein the action comprises enabling the surgical system to use the surgical tool in a surgical operation.

17. The computer-readable storage device of claim 15, wherein the status result is that the status list does not include the tool data, and wherein the action comprises enabling the surgical system to use the surgical tool based on the status list not including the tool data.

18. The computer-readable storage device of claim 15, wherein the status result is that the status list includes the tool data, and wherein the action comprises disabling at least one function of the surgical tool based on the status list including the tool data.

19. The computer-readable storage device of claim 15, wherein the status list is maintained on a remote computing device and communicated to the surgical system in response to an update to the status list.

20. The computer-readable storage device of claim 15, wherein the status list comprises a whitelist describing an identity and an authorization status of the plurality of surgical tools coupleable to at least one robotic arm of a robotic surgical system, the authorization status confirming the robotic surgical system is enabled to use the plurality of surgical tools on the whitelist.

21. The computer-readable storage device of claim 15, wherein the status list comprises a blacklist describing an identity and an authorization status of the plurality of surgical tools coupleable to at least one robotic arm of a robotic surgical system, the authorization status confirming the robotic surgical system is not enabled to use the plurality of surgical tools on the blacklist.

22. A computer-implemented method, comprising:
prior to coupling a surgical tool to a surgical system, receiving, from a remote computing system and at a computing device of the surgical system, a first device key that is specific to the surgical tool;
storing, in a memory of the computing device of the surgical system, the first device key specific to the surgical tool coupled to the surgical system;

receiving, via a communication device of the computing device and from the surgical tool, an authentication message encrypted with a second device key;

authenticating, at the computing device, the authentication message based on decrypting the authentication message with the first device key;

receiving, at the computing device and from the surgical tool, tool data comprising an identifier of the surgical tool;

determining a status result based on the identifier and a surgical tool blacklist, the status result identifying a match between the identifier and a portion of the surgical tool blacklist, the surgical tool blacklist comprising identifiers and status data describing an allowed or disallow status of each surgical tool;

disabling at least one function of the surgical system based on the status result and providing information about the status result to the remote computing system.

23. The computer-implemented method of claim 22, wherein disabling at least one function of the surgical tool comprises outputting a notification in response to the match between the identifier and the portion of the surgical tool blacklist.

24. The computer-implemented method of claim 22, further comprising disabling operation of the surgical tool based on the status result.

25. The computer-implemented method of claim 22, further comprising disabling operation of a robotic arm of the surgical system connected to the surgical tool.

26. The computer-implemented method of claim 22, further comprising generating an entry of the surgical tool blacklist in response to a first identifier of a first surgical tool identified in use in a plurality of locations.

27. The computer-implemented method of claim 22, further comprising generating an entry of the surgical tool blacklist in response to a tool use counter for a particular surgical tool exceeding a predetermined threshold.

28. The computer-implemented method of claim 22, further comprising generating an entry of the surgical tool blacklist in response to a tool recall status for a particular type of surgical tools.

29. A computer-implemented method, comprising:

providing, to a robotic surgical system, a first device key that is specific to a first surgical tool, wherein the first device key is configured to enable authentication of the first surgical tool;

storing, at an authentication server, a status list comprising identification data and status data for a plurality of surgical tools;

storing, at the authentication server, a tool use dataset comprising the identification data and location data associated with the plurality of surgical tools, the location data representative of locations at which the plurality of surgical tools have been used;

receiving tool connection data from the robotic surgical system, the tool connection data describing a first identity of the first surgical tool and a first location of the first surgical tool in response to the first surgical tool being connected to the robotic surgical system and authenticated by the robotic surgical system;

determining a result based on the tool connection data and the tool use dataset;

generating an updated status list based on the result; and transmitting the updated status list to a plurality of different robotic surgical systems, wherein the plurality of different robotic surgical systems are configured to use the updated status list to authenticate surgical tools; and providing information about the result to a remote system.

30. The computer-implemented method of claim 29, wherein the status list comprises an operational status or a blocked status for each of the plurality of surgical tools, the operational status for a respective surgical tool indicating that a respective robotic surgical system will be enabled to use the respective surgical tool, the blocked status for the respective surgical tool indicating that the respective robotic surgical system will not be enabled to use the respective surgical tool.

31. The computer-implemented method of claim 29, wherein the result is that the tool use dataset includes the first identity of the first surgical tool associated with a second location of the first surgical tool, and wherein updating the status list comprises changing a status of the first surgical tool to a blocked status to prevent use of the first surgical tool.

32. The computer-implemented method of claim 29, wherein transmitting the updated status list comprises updating entries in a local status list of each of the plurality of different robotic surgical systems.

33. The computer-implemented method of claim 29, wherein the status list comprises tool usage data indicating at least one of an operational life of each of the plurality of surgical tools, a usage time of each of the plurality of surgical tools, or an expiration date of each of the plurality of surgical tools.

34. The computer-implemented method of claim 29, wherein the tool connection data comprises tool use information indicating a use of the first surgical tool.

35. The computer-implemented method of claim 29, wherein updating the status list comprises updating the tool use dataset, and the method further comprises changing the status of the first surgical tool to a blocked status in response to a value of the tool use dataset exceeding a predetermined threshold.

* * * * *